United States Patent [19]

Amon, Jr. et al.

[11] 4,423,149

[45] * Dec. 27, 1983

[54] PROCESS FOR THE PRODUCTION OF D-GLUCOSONE

[75] Inventors: William F. Amon, Jr., Danville; John Geigert, Clayton; Saul L. Neidleman, Oakland, all of Calif.

[73] Assignee: Cetus Corporation, Berkeley, Calif.

[*] Notice: The portion of the term of this patent subsequent to Jan. 20, 1998, has been disclaimed.

[21] Appl. No.: 311,505

[22] Filed: Oct. 15, 1981

[51] Int. Cl.$^3$ .................... C12P 19/02; C12P 7/26; C12P 7/60; C12P 7/00

[52] U.S. Cl. .................... 435/105; 435/148; 435/138; 435/132

[58] Field of Search .................... 435/105, 148

[56] References Cited

U.S. PATENT DOCUMENTS

| | | | |
|---|---|---|---|
| 4,246,347 | 1/1981 | Neidleman et al. | 435/105 |
| 4,247,641 | 1/1981 | Neidleman et al. | 435/123 |
| 4,321,323 | 3/1982 | Maselli et al. | 435/105 |
| 4,321,324 | 3/1982 | Maselli et al. | 435/105 |
| 4,351,902 | 9/1982 | Neidleman et al. | 435/137 |

OTHER PUBLICATIONS

R. Selby, et al., *J. Chem. Soc.*, 75, 787–792 (1899).
W. L. Evans, et al., *J. Amer. Chem. Soc.*, 50, 2267–2285 (1928).
*Advances in Carbohydrate Chemistry*, vol. II, edited by M. L. Wolfrom, 1956, pp. 43–96.
H. J. Hass and P. Schlimmer, *Liebigs Ann. Chem.*, 759, 208 (1972).
C. Berkeley, *Biochem. J.*, 27, 1357–1365 (1933).
C. R. Bond, E. C. Knight and T. K. Walker, *Biochem. J.*, 31, 1033–1040 (1937).
R. C. Bean and W. Z. Hassid, *Science*, 124, 171 (1956).
F. W. Janssen and H. W. Ruelius, *Biochem. Biophys. Acta*, 167, 501–510 (1968).
J. Volc, M. Wurst and V. Musilek, *Folia Microbiol.*, 23, 448–452 (1978).
Z. Diwnjak and M. D. Lilly, *Biotechnology and Bioengineering*, 18, 737–739 (1976).
Y. K. Cho and J. E. Bailey, *Biotechnology and Bioengineering*, 19, 769–775 (1977).

*Primary Examiner*—Lionel M. Shapiro
*Attorney, Agent, or Firm*—Fitch, Even, Tabin & Flannery

[57] ABSTRACT

A process is described for the production of D-glucosone from glucose. An aqueous solution of glucose is converted substantially completely to D-glucosone by an enzymatic oxidation while removing or utilizing co-produced hydrogen peroxide. D-glucosone is a useful intermediate product which may then be converted to a desired end product.

12 Claims, No Drawings

PROCESS FOR THE PRODUCTION OF D-GLUCOSONE

This invention relates generally to the production of D-glucosone from glucose by way of enzymatic oxidation. This process provides a novel approach for the production of substantially pure D-glucosone without the necessity for physical separation of the residual glucose starting material.

The unique physical and chemical properties of D-glucosone present the possibility of pathways to certain end products which pathways are unique and advantageous. For example, substantially pure D-glucosone may be readily converted to pure fructose, a useful sweetener which is about 50% sweeter than sucrose and which can be used at lower levels to give the same sweetness. Such a process is described in U.S. Pat. No. 4,246,347, assigned to the assignee of the present invention.

The prior art teaches that low levels of D-glucosone can be made from glucose. Several methods of oxidizing glucose have been reported—with $H_2O_2$ (R. Selby, M. A. Morrell and J. M. Crofts, *J. Chem. Soc.*, 75, 787 (1899)), or with copper acetate (W. L. Evans, W. D. Nicoll, G. C. Strouse and C. E. Waring, *J. Amer. Chem. Soc.*, 50, 2267 (1928)). In each of these reactions, conversion yields are low (<30%) and many side-products arise. Glucose has been converted to D-glucosone by first preparing a derivative of the glucose (e.g. by reacting with phenyl hydrazine to make glucosazone, see *Advances in Carbohydrate Chemistry*, Vol. II, edited by M. L. Wolfrom, 1956, pp. 43–96, or reacting with p-toluidine, see H. J. Hass and P. Schlimmer, *Liebigs Ann. Chem.*, 759, 208 (1972)), and then chemically treating that derivative to yield D-glucosone. In these reactions, yields were no higher than 50%, and the unrecoverable reagents are too expensive for commercial use. In addition, the use of aromatic-containing reagents could pose problems in achieving food grade quality sugars.

Conversion of glucose to D-glucosone is also a known enzymatic reaction. As early as 1932, glucose was reported to be oxidized to D-glucosone by the crystalline style of a mollusca, *Saxidomus giganteous*, see C. Berkeley, *Biochem. J.*, 27, 1357 (1933). In 1937, D-glucosone was reported to be formed by the oxidation of glucose, starch, maltose or sucrose with plasmolysed preparations of two molds, *Aspergillus parasiticus* and *Aspergillus flavus-oryzae*, see C. R. Bond, E. C. Knight and T. K. Walker, *Biochem. J.*, 31, 1033 (1937). In 1956, the enzymatic oxidation of glucose to D-glucosone was reported in a red alga, *Iridophycus flaccidum*, see R. C. Bean and W. Z. Hassid, *Science*, 124, 171 (1956). A carbohydrate oxydase was isolated from mycelia of the Basidiomycete, *Polyporous obtusus*, which oxidized glucose to D-glucosone, see F. W. Janssen and H. W. Ruelius, *Biochem. Biophys. Acta*, 167, 501 (1968). No mention was made of yields. Finally, in 1978, glucose-2-oxidase activity was detected in the basidiomycete, *Oudemansiella mucida*, as well as other wood-rotting fungi, see J. Volc, M. Wurst and V. Musilek, *Folia Microbiol.*, 23, 448 (1978). The best yield reported was no higher than 50%. In all of these cases D-glucosone production, it is believed, is accompanied by generation of hydrogen peroxide.

One of the objects of the present invention is to provide an improved method for producing substantially pure D-glucosone from glucose.

Another object of the present invention is to provide a D-glucosone-making process in which the costly physical separation of residual glucose from D-glucosone or from a D-glucosone-rich syrup is unnecessary.

A further object of the invention is to provide a process by which pure D-glucosone may be made from glucose in an economical and commercially feasible way.

Other objects of the present invention will become apparent from the following description and examples.

As used herein, the terms "glucose", "D-glucose" and "dextrose" are employed interchangeably to embrace this monosaccharide in any form—solution or dry.

As used herein, the terms "D-glucosone" and "D-arabino-2-hexosulose" are employed interchangeably.

As used herein, the terms "fructose", "D-fructose" and "levulose" are employed interchangeably to refer to the isomer of glucose that is sweeter than glucose. The term "crystalline fructose" is used in this application to embrace this monosaccharide in anhydrous form.

According to the present invention, generally stated, glucose in aqueous solution is enzymatically converted to D-glucosone with an appropriate enzyme such as pyranose-2-oxidase or glucose-2-oxidase. This conversion is allowed to proceed spontaneously, rapidly and substantially completely. The resulting D-glucosone substantially free of glucose and all other saccharides, is recovered either as an aqueous solution or in semi-solid form.

As mentioned and referenced above, low level enzymatic conversions of glucose to D-glucosone are known in the scientific literature, but the concept of allowing this reaction to go to substantial completion to produce D-glucosone from glucose has not been obvious to others. In addition, the successful use of this reaction coupled with a further reaction to produce an economic, commercially useful product has not been reported prior to our invention. In the reported conversion of glucose to D-glucosone, the concept of enzymatically producing substantially pure D-glucosone from glucose was not considered. D-glucosone was chemically synthesized because it was desired as a chemical standard. D-glucosone was discovered in biological systems, either unintentionally (e.g. as an unknown component in a biochemical pathway under study) or intentionally (e.g. as part of an investigation of the biochemical oxidation of glucose in blood).

Unless the conversion of glucose to D-glucosone is accomplished in high yield, the industrial production of further products from the D-glucosone would be prohibitive since the costly physical separation treatment to remove residual glucose would still be needed. According to the present invention, glucose is readily and completely converted to D-gluocosone using a purified oxidoreductase enzyme such as pyranose-2-oxidase or glucose-2-oxidase. The yield obtained in the present invention exceeds that reported in the literature for this enzyme. This high conversion to D-gluocosone eliminates the need to physically separate any residual unconverted glucose.

Certain oxidoreductases have catalytic activity with respect to oxidizing the hydroxyl group on the second carbon of glucose, promoting oxidation of that hydroxyl group to a keto group. The specific oxidoreductase enzymes described in the examples herein are referred to variously as "glucose-2-oxidase", "pyranose-2- oxidase", and "carbohydrate oxidase", but the invention is not necessarily limited to enzymes so designated. Glucose-2-oxidase possesses a high specificity for glucose as a substrate, whereas carbohydrate oxidase, while having glucose as its preferred substrate, has a broader substrate specificity. Any enzyme capable of converting the hydroxyl group on the second carbon of glucose to a keto group and not otherwise substantially affecting the remainder of the glucose molecule falls within the scope of our invention. Such an enzyme may be specified as one which has glucose-2-oxidase activity.

A preferred pyranose-2-oxidase enzyme is derived from the microorganism *Polyporus obtusus*. Sources of glucose-2-oxidase include several other microorganisms, millusca and red alga referred to above. These enzymes and their sources are merely indicative and are not intended to be all-inclusive of suitable enzymes and their sources within the scope of this invention.

For ease of discussion, various aspects of the present invention will be described with particularity, but not exclusivity, in connection with the use of the preferred pyranose-2-oxidase of *Polyporus obtusus* and the glucose-2-oxidase of *Aspergillus oryzae*. The microoganisms may be grown in agitated, submerged culture at room temperature by conventional methods. The enzyme is prepared from the mycelia of the microorganism grown under agitated, submerged culture conditions.

The enzyme is preferably used in an immobilized form, although free enzyme can also be used. The processes for enzyme immobilization are familiar to those skilled in the art, and consist of reacting a solution of the enzyme with one of a broad range of surface treated or untreated organic and inorganic supports. Included among these are polyacrylamide, ethylenemaleic acid copolymers, methacrylic-based polymers, polypeptides, styrene-based polymers, agarose, cellulose, dextran, silica, porous glass beads, charcoal or carbon black, hydroxy apatite and aluminum or titanium hydroxide. Enzymes in this form have increased stability, extended life and usefulness and recoverability. Reactions employing immobilized enzymes may be run in columns or reaction tanks or other suitable reactors.

In addition to the pyranose-2-oxidase or glucose-2-oxidase enzymes, a source of oxygen is needed. Also, a method of hydrogen peroxide removal or utilization is required in the reaction to convert glucose to D-glucosone most efficiently. This is because $H_2O_2$ oxidizes certain critical sites on the enzyme molecule, damaging its function. Procedures of hydrogen peroxide removal include (1) decomposition by the enzyme, catalase, (2) decomposition by known chemical means, and (3) decomposition by using decomposing matrices such as manganese oxide or carbon black (see Z. Diwnjak and M. D. Lilly, *Biotechnology and Bioengineering*, 18, 737–739, (1976); and Y. K. Cho and J. E. Bailey, *Biotechnology and Bioengineering*, 19, 769–775, (1977)) as the immobilizing support for the oxidoreductase enzyme. In a preferred alternative method, the hydrogen peroxide produced, rather than being decomposed, may be consumed to produce a valuable co-product. Coupling D-gluocosone production with propylene halohydrin or propylene oxide production, in accordance with U.S. Pat. No. 4,247,641 is one example.

The enzymatic conversion of glucose to D-glucosone is preferably conducted in water at about neutral pH, but can be conducted within the pH range of from about three to about eight with the use of appropriate buffers. This conversion is preferably conducted at ambient temperature, but can be conducted within the temperature range of from about 15° C. to about 65° C. Pressure conditions are preferably atmospheric but can range from below to above atmospheric. Any carbohydrate material, which by chemical or enzymatic means yields glucose, is a suitable source of glucose for conversion to D-glucosone. These substances would include, but are not limited to the following: cellulose, starch, sucrose, corn syrup, HFCS and other syrups containing varying proportions of glucose and fructose.

After conversion of substantially all of the glucose to D-glucosone, the D-glucosone may be readily and essentially completely converted to a further product. One example of this step is conversion to fructose using molecular hydrogen and an appropriate catalyst as described in U.S. Pat. No. 4,246,347. Another example of this step is conversion to 2-keto-D-gluconic acid using the enzyme glucose-1-oxidase as described in U.S. patent application Ser. No. 160,122, filed June 16, 1980.

The assays used for analyzing the sugars of the present invention are given below:

1. Thin layer chromatography (TLC)—Avicel coated glass plates are developed with an 8:8:2:4 (by volume); isopropanol:pyridine:acetic acid:water solvent system. Glucose has $R_f$'s 0.5–0.6; D-glucosone has an $R_f$ 0.4–0.5 streak. ($R_f$=the distance substance migrates from origin/solvent front distance from origin). When the plates are sprayed with triphenyltetrazolium chloride (2% TTC in 0.5 N NaOH), D-glucosone instantly yields a red spot; glucose yields a red spot only upon heating for ten minutes at 100° C. When the plates are sprayed with diphenylamine/aniline/phosphoric acid-/ethyl acetate reagent, (0.15 g/0.8 ml/11 ml/100 ml), glucose yields a brown spot; D-glucosone yields a purple streak upon heating for 10 minutes at 95° C.

2. High performance liquid chromatography (HPLC)—A $\mu$-Bondapak-Carbohydrate column, purchased from Waters Associates, is run with 15% aqueous acetonitrile at a flow rate of 2 ml/min. Glucose has a $R_t$ 11.5, and D-glucosone a $R_t$ 14.0, ($R_t$=retention time). Assays are run on a Spectra Physics SP8000 instrument using both a Waters Associates refractive index detector and a Schoeffel variable wavelength UV detector set at 192 nm.

3. Mass spectrometry (MS)—The following derivatization protocol is used to make the chemical components volatile:

(a) To approximately 100 mg of the lyophilized sample, 110 mg of N,N-diphenylhydrazine ($H_2NN\phi_2$) and 1 ml of 75% aqueous ethanol are added. The reaction mixture is vortexed and then allowed to sit overnight at room temperature.

(b) 3 ml of water is added to the reaction mixture and the resulting precipitate is separated from the supernatant by centrifuging and decanting. To this precipitate, 1 ml of a 1:1 mixture of pyridine-acetic anhydride is added. The reaction mixture is placed in a 35°–40° C. water bath for 15 minutes, with occasional shaking.

(c) 2 ml of water is added to stop the reaction and then the mixture is extracted 2 times with 3 ml portions of ethyl ether. The ether is dried over a small amount of anhydrous sodium sulfate, then the ether is driven off with gentle heating (−40° C.) and blowing nitrogen.

(d) The resulting solid or syrup is ready for mass spectrometric analysis.

Expected reactions

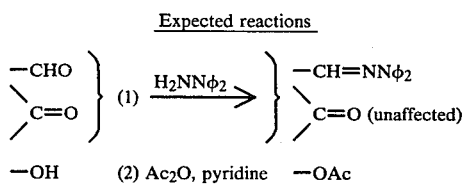

Glucose yields a molecular ion at mass 556 ($C_{28}H_{32}N_2O_{10}$) and a base ion at mass 168 ($N\phi_2$ ion fragment); D-glucosone yields a molecular ion at mass 512 ($C_{26}H_{28}N_2O_9$) and an intense, diagnostic fragment ion at mass 223 (OC—CH=N—N$\phi_2$ ion fragment). Assays are run on a Finnigan GC/MS/DS Model 4021 instrument set at 70 eV electron impact ionization and at 220° probe temperature.

4. Colorimetric test tube assay—The analysis of D-glucosone in the presence of an excess of glucose is readily determined by two colorimetric methods. Using triphenyltetrazolium chloride (TTC), the detection method is based on a differential rate of reduction by the two sugars. Into a 20 ml test tube is added 0.5 ml sample, plus 0.1 ml 1% aqueous TTC, plus 0.4 ml 6 N NaOH. After exactly 5 min, 15 ml acetic acid:ethanol (1:9) is added and the test tube contents vortexed. With water used as a blank, absorbance is measured at 480 nm, using a Varian 635 UV/VIS spectrophotometer. Glucose reduces TTC to a red pigment—a triphenylformazan—about 100 times slower than an equivalent amount of D-glucosone. Using diphenylamine/aniline/phosphoric acid reagent, the detection method is based on the different colors produced with sugars of different structures. Into a 20 ml test tube is added B 0.2 ml sample, plus 5 ml of the following reagent mix:

diphenylamine: 0.15 g
aniline: 0.80 ml
isopropanol: 100 ml
phosphoric acid: 11 ml The test tubes are placed in 37° water bath for 60 minutes. Glucose yields a yellow-colored solution; D-glucosone yields a purple-colored solution.

The sources of the pure sugars used in various analytical aspects of the invention are given below:

1. D-glucose was purchased from Applied Science Laboratories, 99% purity,

2. D-glucosone was chemically synthesized by the following method: 20 g of glucose is mixed with 1 l of distilled water containing 27 ml glacial acetic acid. 44 g of phenylhydrazine is added. The reaction is run for 3 hours at 80° C. with vigorous stirring from a mechanical stirrer and then cooled to room temperature overnight. The solid is filtered and washed with 10% acetic acid, water, and then ethyl ether. The solid is dried well in a vacuum oven at 50° C. Experimental yield is 16.1 g of glucosazone. The glucosazone is placed in a 3-neck, 3-l flask and 450 ml of ethanol, 750 ml of distilled water and 9 ml glacial acetic acid are added. 27.8 of fresh benzaldehyde is added and brought to reflux while vigorously stirring with a mechanical stirrer. The reaction is refluxed for 5 hours. The condenser is reversed and 450 ml is distilled over, while adding 750 ml of distilled water (via an addition funnel) to the flask. The reaction is cooled overnight to let the benzaldehyde phenylhydrazine precipitate. The solution is filtered and the residue washed with distilled water (~1 l) until the water becomes clear. The filtrate plus washings are concentrated to 500 ml and then extracted with 10 by 300 ml portions of ethyl ether. To get rid of residual ethyl ether in the aqueous solution, it is placed on a rotary evaporator for 30 minutes. The aqueous solution is passed through a 4 by 100 cm column containing rigorously acetone-washed Amberlite XAD-2. The column is washed with an additional 200 ml of water to remove residual D-glucosone. The combined aqueous portions are lyophilized. Experimental yield of D-glucosone is 3.4 g (16% overall yield).

The following examples illustrate various features of the invention, but are in no way intended to limit the scope of the invention which is defined in the appended claims. Unless indicated otherwise, all temperatures are at ambient temperature (about 25° C.) and all pressures at ambient room pressure (about 1 atm).

EXAMPLE I

Substantially complete conversion of glucose to D-glucosone using immobilized pyranose-2-oxidase is shown in this example.

Glucose (2 g) is added to 20 ml of distilled water in a 100 ml Pyrex flask and the sugar solution stirred. Oxygen gas is bubbled into the flask and 3 mg of catalase (Sigma Chemical Co., C-40, from bovine liver) is added. Agarose-immobilized pyranose-2-oxidase prepared as below is also added to the flask.

To prepare the enzyme, mycelial pads of *Polyporus obtusus* ATCC#26733 are grown on yeast/malt extract agar slants as follows: yeast extract (3 g), malt extract (3 g), agar (20 g), peptone (5 g) and glucose (10 g) are added to distilled water (1 l) and the pH is adjusted to 6.7. The medium is sterilized at 121° C. for 15 minutes. The pH is then adjusted to 6.4. The organism is inoculated on the agar slants and grown for 7 days at 25° C. The slant-grown organism is then used to inoculate yeast/malt extract medium (20 ml medium in 125 ml Erlenmeyer flask), prepared as above (but no agar added). The organism is grown for 9 days on a rotary shaker at 25° C. The culture is vacuum filtered through #541 Whatman paper in a Buchner funnel. The mycelia, retained on the filter paper, contain the enzyme.

The mycelia obtained from 400 ml of culture are washed twice with 0.05 M potassium phosphate buffer at pH 7.0. The mycelia are then placed in a Waring blender which contains 70 ml of 0.05 M potassium phosphate buffer at 7.0, and then homogenized for 3 minutes. The mixture is then centrifuged at 6000 rpm for 20 minutes and the supernatant decanted from the solids. To the supernatant, placed in a 500 ml Erlenmeyer flask, 19 g of polyethylene glycol (weight 4000) is added and the solution stirred for 30 minutes. The suspension is then centrifuged at 7000 rpm for 20 minutes. The supernatant is decanted off and discarded. 15 ml of 0.2 M sodium chloride plus 15 ml of 0.05 M potassium phosphate buffer at pH 7.0 are then added to the precipitate and vortexed. The solution is allowed to stand for 30 minutes during which time a precipitate forms. The mixture is centrifuged at 14000 rpm for 20 minutes. An opaque white supernatant containing cell-free, purified enzyme is decanted off.

Immobilization of the enzymes on agarose may be accomplished as follows: The cell-free purified enzyme is dialyzed against 500 ml of distilled water overnight. Then 5 ml of 0.1 M sodium bicarbonate at pH 8.0 is added. To this solution, 5 g of Activated Ch-Sepharose 4B (washed and reswelled on a sintered glass filter using 500 ml of 1 mM HCl) is added. Using an end-over-end mixer, the gel suspension is mixed for 1 hour at 25° C. The gel suspension is then washed first with 40 ml of 0.1 M sodium bicarbonate at pH 8.0, then with 40 ml of 0.05 M Tris buffer at pH 8.0 containing 0.5 M sodium chloride, and then with 0.5 M sodium formate buffer at pH 4.0 also containing 0.5 M sodium chloride.

Samples of the reaction mixture are withdrawn at varying times and analyzed for glucose and D-glucosone. Using HPLC, the peak areas of the peaks at $R_t$ 11.5 min. (glucose) and $R_t$ 14.0 min. (D-glucosone) are quantitated and levels of sugar present calculated. The following results are obtained:

| Reaction Time | Glucose, g | D-Glucosone, g | % of Glucose converted to D-Glucosone |
| --- | --- | --- | --- |
| 0 hr | 2.0 | 0.0 | 0 |
| 1 | 1.2 | 0.8 | 40 |
| 2 | 0.5 | 1.5 | 75 |
| 3 | 0.2 | 1.8 | 90 |
| 4 | <0.1 | >1.9 | 99+ |

The substantial conversion of glucose to D-glucosone is also shown by the disappearance of the spot at $R_f$ 0.58 (Glucose) and the appearance of the streak at $R_f$ 0.43–0.49 (D-glucosone) over the course of the reaction, and by the increase in absorbance at 480 nm over the course of the reaction using the TTC colorimetric test tube assay.

That the product is indeed D-glucosone is confirmed by derivatization followed by mass spectrometry as described previously. The diagnostic D-glucosone mass ions at mass 512 (molecular ion) and mass 223 (OC—CH=N—N$\phi_2$ ion fragment) are obtained for the product.

EXAMPLE II

The following example illustrates the chemical conversion of D-glucosone to fructose using various catalysts:

D-glucosone (20 mg) is added to 2 ml of distilled water in a micro-hydrogenator apparatus (Supelco, Inc.). Catalyst (50 mg) is then added and the apparatus is fed hydrogen gas—continuously bubbled if at atmospheric pressure, batch fed if at higher than atmospheric pressure.

After 5 hours, the residual D-glucosone and the produced fructose are analyzed.

Using HPLC, the peak areas of the peaks at $R_t$ 14.0 min. (D-glucosone) and $R_t$ 9.5 min. (fructose) are quantitated and levels of sugar present calculated. The following results are obtained:

| Catalyst[a] | Pressure | % D-glucosone Converted to Fructose |
| --- | --- | --- |
| 5% Rhodium on Alumina | atmospheric | 40 |
| 5% Rhodium on Carbon | atmospheric | 50 |
| 5% Platinum on Carbon | atmospheric | 60 |
|  | 55 psi | 70 |
| 10% Platinum on Carbon | atmospheric | 75 |
| Platinum Black | atmospheric | 80 |
| Platinum Oxide | 55 psi | 65 |
| 5% Palladium on Carbon | atmospheric | greater than 90 |
|  | 55 psi | greater than 90 |
| Raney Nickel | atmospheric | 30[b] |

[a]Catalysts were obtained from Engelhard Industries, except for the Raney Nickel which was obtained from Pfaltz and Bauer, Inc.
[b]This catalyst also reduces the produced fructose - an undesired effect.

The conversion of D-glucosone to fructose is also shown by the disappearance of the streak at $R_f$ 0.43–0.49 (D-glucosone) and the appearance of the spot at $R_f$ 0.52.

That the product is indeed fructose is confirmed by derivatization followed by mass spectrometry as described previously. The diagnostic fructose mass ion at mass 390 (molecular ion) is obtained for the product.

EXAMPLE III

Essentially complete conversion of D-glucosone to fructose under varying hydrogenation conditions is shown in this example.

Reaction A

D-glucosone (1 g) is added to 200 ml of distilled water in a micro-hydrogenator apparatus. 5% palladium (Pd) on carbon (1 g) is then added and hydrogen gas is continuously bubbled into the vessel at atmospheric pressure and ambient temperature. After 24 hours, additional 5% palladium on carbon (500 mg) is added. The reaction is ended at 30 hours.

Reaction B

D-glucosone (1 g) is dissolved in 136 ml water and 0.1 g of 5% on carbon is added to the solution. The solution is placed in a pressure vessel equipped with an efficient magnetic stirrer. The apparatus is pressured to 500 psig with $H_2$ after the usual removal of air. The vessel is heated to 130° C. while the contents are vigorously stirred. The calculated amount of $H_2$ is taken up in 75 minutes. After removal of catalyst and evaporation of the water in vacuum, a syrupy residue is left. The product is identified as fructose. In addition, the proton NMR spectrum confirms the absence of mannitol and sorbitol, the products of further reduction.

Reaction C

D-glucosone (2 g) is dissolved in 140 ml 88% aqueous ethanol and reacted as in reaction B. The theoretical amount of $H_2$ is consumed in 16 hours.

The conditions for each reaction and the results obtained are summarized in the following table:

| Reaction | Weight Ratio Catalyst to Glucosone | Solvent | Temp. | Pressure psig | Time hr | % Conversion |
| --- | --- | --- | --- | --- | --- | --- |
| A | 1.5 | $H_2O$ | 25° | 0 | 30 | 95% |
| B | 0.1 | $H_2O$ | 130° | 625 | 1.25 | 100% |
| C | 0.1 | (88:12)EtOH:$H_2O$ | 130° | 575 | 4 | 100% |

It can be seen that the hydrogenation of D-glucosone to fructose can be conducted under a variety of differing protocols involving changes in temperature, pressure, solvent, reaction time and weight ratio of catalyst to substrate. The palladium catalyst does not further reduce fructose.

EXAMPLE IV

The following represents an example for essentially complete conversion of glucose to fructose by the action of immobilized pyranose-2-oxidase, followed by chemical reduction.

Glucose (1 g) is added to 50 ml of distilled water in a 250 ml Pyrex flask and the sugar solution stirred. Agarose-immobilized pyranose-2-oxidase, prepared as in Example I from 50 ml of cell-free, purified enzyme, is then added to the flask, along with 1 mg of catalase (as in Example I).

Eighteen hours later the aqueous solution is decanted from the solids. Analysis of this solution shows that 99+% of the glucose has been converted to D-glucosone.

The aqueous solution is placed in a 100 ml Pyrex flask and stirred. 1 g of 5% palladium on carbon catalyst is added and hydrogen gas bubbling started.

After 24 hours, the aqueous solution is filtered from the solids using Whatman #1 filter paper and Celite filtering aid. Analysis shows that it consists of greater than 95% fructose.

EXAMPLE V

This example shows the production of crystalline fructose from glucose.

The enzymatic conversion of glucose to D-glucosone and the chemical reduction of D-glucosone to fructose yields the aqueous solution of Example IV. This aqueous filtrate is evaporated to dryness under vacuum at 45° C. A white solid material results which rapidly turns into a gummy residue.

This residue is dissolved in 10 ml of hot ethanol, and then the solution is allowed to cool at room temperature for 5 days. White, crystalline material results having the same physical properties (i.e. appearance, melting point and optical rotation) as crystalline fructose; it is crystalline fructose.

EXAMPLE VI

This example shows essentially complete enzymatic conversion of glucose to D-glucosone using glucose-2-oxidase.

The reaction and conditions of Example I (using agarose as the immobilizing support) are repeated substituting glucose-2-oxidase for pyranose-2-oxidase. After 5 hours of reaction, more than 99% of the glucose was converted to D-glucosone.

To prepare the enzyme, glucose-2-oxidase, mycelial cultures of *Aspergillus oryzae* ATTC#7252 are grown in beef, yeast extract/tryptone medium as follows: beef extract (5 g), yeast extract (5 g), tryptone (3 g), dextrose (1 g) and Difco starch (24 g) are added to distilled water (1 l) and the pH adjusted to 7.3. The medium is sterilized at 121° C. for 35 minutes. Using spores obtained in a generally known manner, the medium is inoculated to obtain about $3 \times 10^4$ spores/ml and grown on a rotary shaker (180 rpm) at 30° C. for 2 days. The culture is vacuum filtered through #541 Whatman paper in a Buchner funnel and washed several times with water. The mycelia, retained on the filter paper, contain the enzyme.

Purification and immobilization of the enzyme can then proceed using the procedure of Example I.

EXAMPLE VII

In Example I, the level of free hydrogen peroxide generated by the reaction of glucose with pyranose-2-oxidase in conjunction with D-glucosone formation was minimized by using catalase to decompose the hydrogen peroxide. An alternative method of minimizing the level of free hydrogen peroxide is to couple its production to a hydrogen peroxide-utilizing reaction yielding a desirable (valuable) co-product.

In this example, hydrogen peroxide production is coupled to the production of propylene bromohydrin, an intermediate in propylene oxide synthesis according to concepts detailed in U.S. Pat. No. 4,247,641. The reaction of glucose and the immobilized pyranose-2-oxidase of *Polyporus obtusus* ATCC #26733 to yield D-glucosone and hydrogen peroxide is coupled to the reaction of immobilized seaweed peroxidase from Coralina sp. in the presence of bromide and propylene to yield propylene bromohydrin. The end result of this coupled reaction, then, is the co-production of D-glucosone for subsequent fructose production and of propylene bromohydrin, readily converted to propylene oxide as described in U.S. Pat. No. 4,247,641. Any enzyme capable of oxidizing the hydroxyl group on the 2-carbon of glucose with associated production of hydrogen peroxide can be coupled to any halogenating peroxidase and the composite used for alkene halohydrin production following the teachings of our aforereferenced co-pending patent applications.

Cell-free, purified seaweed peroxidase enzyme is prepared as follows:

Coralina sp. obtained along the coast of La Jolla, Calif., is ground in a Virtis 45 homogenizer for 5 minutes in distilled water. The homogenate is spun at 20,000 rpm for 20 minutes. The supernatant is decanted and saved. The pellet is resuspended in distilled water and recentrifuged. This supernatant and previous supernatant are combined. The solution is brought first to 33%, then to 55% saturation in ammonium sulfate. Centrifugation and separation of pellet is performed at each step. The 33%–55% pellet fraction is passed through a DEAE column using a 0.3 M to 1 M phosphate buffer (pH 6.0) gradient. The fraction which elutes at 1 M is dialyzed against 20 mM phosphate buffer (pH 6) overnight.

The immobilized seaweed peroxidase is prepared as follows:

Glass beads (obtained from Sigma Chemical Company, PG-700-200) are activated by suspending 1 g of glass beads in 18 ml of deionized water. 2 ml of 10% (v/v)α-aminopropyltriethoxy silane are added and the pH of the mixture is adjusted to 3–5 with 6 N HCl. The mixture is shaken at 75° C. for two hours. The glass beads are then vacuum dried overnight at 80° C. 3.2 ml of purified Coralina sp. enzyme, prepared as above, and 50 mg of water soluble carbodiimide are added to the glass beads. The pH is adjusted to 4.5, and the mixture is then shaken at 4° C. overnight. The product (enzyme coated beads) is washed with water. The activity is measured as 2 monochlorodimedon units/g of beads.

Immobilized pyranose-2-oxidase on agarose is prepared as in Example I from 10 ml of cell-free, purified enzyme.

A reaction mixture containing the following ingredients is set up in a 100 ml Pyrex flask:
(a) 1 g seaweed peroxidase coated glass beads, (b) the immobilized pyranose-2-oxidase prepared above,
(c) 800 mg potassium bromide, and
(d) 20 ml of 0.01 M potassium phosphate buffer, pH 7.0.

Both propylene and oxygen are bubbled into the flasks continuously. The reaction is initiated with 1 gm glucose. After 20 hours the reaction is sampled and analyzed for residual glucose, D-glucosone, and propylene bromohydrin. The produced propylene bromohydrin is analyzed as follows:

5 $\mu$l of the reaction mixture is injected into a Hewlett-Packard Model 402 gas chromatograph, equipped with a 6 foot by ⅛-inch glass column, packed with Porapak R (80/100 mesh). Flow rate is set at 30 ml/minute for helium and the column temperature is set at 200° C. Retention times for the propylene bromohydrins are 9 minutes for 1-bromo-2-propanol and 10 minutes for 2-bromo-1-propanol.

Product identity is confirmed by comparison with authentic samples of propylene bromohydrin: 1-bromo-2-propanol is purchased from Pfaltz and Bauer, Inc.; 2-bromo-1-propanol is synthesized by lithium aluminum hydride reduction of 1-bromopropionyl chloride. The reaction products and the authentic samples show the same retention times and identical mass spectra: bromine is identified by the presence of the M and M+2 isotope clusters of equal intensity; the molecular ion for both isomers is confirmed by chemical ionization with isobutane reagent gas (M+; m/e 138+140); for 1-bromo-2-propanol the major fragmentation is the expected loss of $CH_2Br$, while for 2-bromo-1-propanol the major fragmentation is the expected loss of $CH_3CHBr$.

The analysis of the sample showed >99% conversion of glucose to D-glucosone and propylene bromohydrin production at 20 gm/l.

EXAMPLE VIII

This example serves to further illustrate the concepts set forth and shown in Example VII. In this instance, immobilized glucose-2-oxidase is substituted for immobilized pyranose-2-oxidase.

The immobilized seaweed peroxidase enzyme is prepared as in Example VII. The immobilized glucose-2-oxidase is prepared as in Example VI.

A reaction mixture is set up as in Example VII, substituting immobilized glucose-2-oxidase for immobilized pyranose-2-oxidase.

After 20 hours, the reaction is sampled and analyzed for residual glucose, D-glucosone, and propylene bromohydrin. The results showed >99% conversion of glucose to D-glucosone and propylene bromohydrin production at 19.5 gm/l.

EXAMPLE IX

This example illustrates high conversion of glucose to D-glucosone over an extended time period using immobilized pyranose-2-oxidase in a column reactor.

Pyranose-2-oxidase (cell-free, purified enzyme) (10 ml), prepared as in Example I, is immobilized on hydroxy-apatite (calcium phosphate hydroxide) as follows:

To 100 ml of cell-free, purified enzyme, 20 g of hydroxy-apatite in 100 ml of 1 mM potassium phosphate buffer at pH 7.0 is added. The mixture is stirred for 30 minutes, then the solids are separated from the liquid by decanting, and the solids washed first with 200 ml of 10 mM potassium phosphate buffer at pH 7.0, then with 200 ml of distilled water.

This material is then packed in a glass column (0.5 cm×4.5 cm). A 1% glucose solution is passed through the column at a flow rate of 1.5 ml per hour. The eluant is periodically analyzed for residual glucose and produced D-glucosone.

The eluant, continuously produced in 5 days of running, showed that >95% of the glucose was converted to D-glucosone. No hydrogen peroxide was detected. The study was terminated before the true enzyme half-life was determined. At the slow flow rate of this experiment both oxygen availability and absence of accumulated hydrogen peroxide contributed to the substantially complete conversion of glucose to D-glucosone. In this case the supporting matrix, hydroxy-apatite, caused hydrogen peroxide decomposition.

EXAMPLE X 2-keto-D-gluconic acid is a commercial product useful, for example, as an intermediate for producing other useful end products such as furfural.

This example demonstrates the production of 2-keto-D-gluconic acid (2KGA) from D-glucosone using glucose-1-oxidase. In this example, the utilization of the produced hydrogen peroxide in a co-process is simulated by decomposition with the enzyme, catalase.

D-glucosone (1 g) is added to 20 ml of 0.2 M potassium phosphate buffer (pH 6.0) in a 100 ml Pyrex flask and the sugar solution stirred. Oxygen gas is continuously bubbled into the flask. Catalase (1 mg) purchased from Sigma Chemical Company (No. C10, purified powder from bovine liver) is added. Glucose-1-oxidase (0.1 ml; 1000 units/ml) purchased from Sigma Chemical Company (No. G6500, prepared from *Aspergillus niger*) is added.

Samples are withdrawn and analyzed for residual D-glucosone and produced 2-keto-D-gluconic acid. High-performance liquid chromatography is used to analyze the results. A $\mu$-Bondapak-Carbohydrate column, purchased from Waters Associates, is attached to a Waters Associates HPLC instrument containing dual detectors—refractive index and UV/VIS ($\lambda$192 nm). The mobile phase is 20% aqueous acetonitrile containing 0.003 M potassium phosphate buffer (pH 6) and is passed through the column at 2 ml/min.

An authentic sample of 2KGA (purchased from Sigma Chemical Company) is run for comparison. D-glucosone has a retention time at 15 minutes, and 2KGA at 11 minutes. Residual substrate and product formed are quantitated using peak areas at UV $\lambda$192 nm.

The following results are obtained:

| Reaction Time | Approximate Yield of 2KGA | Approximate % of D-Glucosone Converted to 2KGA |
| --- | --- | --- |
| 0.4 hr | 22 mg | 2 |
| 2 | 343 | 33 |
| 6 | >1050 | >96 |

Essentially complete conversion of D-glucosone to 2-keto-D-gluconic acid is obtained.

EXAMPLE XI

This example demonstrates the production of 2-keto-D-gluconic acid from D-glucose via D-glucosone. In this example, utilization of the produced hydrogen peroxide in a co-process is simulated by decomposition with the enzyme, catalase.

D-glucose (1 g) is added to 20 ml of 0.2 M potassium phosphate buffer (pH 6) in a 100 ml Pyrex flask and the sugar solution stirred. Oxygen gas is continuously bubbled into the flask. 3 mg of catalase (Sigma Chemical Company, purified powder from bovine liver) is added. Agarose-immobilized pyranose-2-oxidase (5 g wet weight) prepared as in Example I is also added to the flask.

Samples of the reaction mixture are withdrawn at varying times and analyzed for D-glucose and D-glucosone using the HPLC method described in Example I. The peak areas of the peaks at retention time 11.5 minutes (D-glucose) and at retention time 14.0 minutes (D-glucosone) are quantitated using the refractive index (RI) detector.

The following results are obtained:

| Reaction Time | Approximate Yield of D-Glucosone | Approximate % of D-Glucose Converted to D-Glucosone |
| --- | --- | --- |
| 0.1 hr | 30 mg | 3 |
| 1 | 418 | 42 |
| 2 | 745 | 75 |
| 4 | >996 | >99 |

Essentially complete conversion of D-glucosone is obtained.

At this point, glucose-1-oxidase (0.1 ml; 1000 units/ml) purchased from Sigma Chemical Company (prepared from *Aspergillus niger*) is added.

Samples of the reaction mixture are withdrawn at varying times and analyzed for D-glucosone and 2-keto-D-gluconic acid using the HPLC method described in Example X. The peak areas of the peaks at retention time 15 min. (D-glucosone) and at retention time 11 min. (2KGA) are quantitated using the UV detector set at $\lambda$192 nm.

The following results are obtained:

| Reaction Time | Approximate Yield of 2KGA | Approximate % of D-Glucosone Converted to 2KGA |
| --- | --- | --- |
| 0.4 hr | 18 mg | 2 |
| 2 | 287 | 30 |
| 6 | >993 | >96 |

Essentially complete conversion of D-glucosone to 2-keto-D-gluconic acid is obtained.

Thus, essentially complete conversion of D-glucose to 2KGA is obtained.

Various modifications of the invention in addition to those shown and described herein will become apparent to those skilled in the art from the foregoing description. Such modifications are intended to fall within the scope of the appended claims.

REFERENCES

1. R. Selby, M. A. Morrell and J. M. Crofts, *J. Chem. Soc.*, 75, 787 (1899).
2. W. L. Evans, W. D. Nicoll, G. C. Strouse and C. E. Waring, *J. Amer. Chem. Soc.*, 50, 2267 (1928).
3. *Advances in Carbohydrate Chemistry*, Vol. II, edited by M. L. Wolfrom, 1956, pp. 43–96.
4. H. J. Hass and P. Schlimmer, *Liebigs Ann. Chem.*, 759, 208 (1972).
5. C. Berkeley, *Biochem. J.*, 27, 1357 (1933).
6. C. R. Bond, E. C. Knight and T. K. Walker, *Biochem. J.*, 31, 1033 (1937).
7. R. C. Bean and W. Z. Hassid, *Science*, 124, 171 (1956).
8. F. W. Janssen and H. W. Ruelius, *Biochem. Biophys. Acta*, 167, 501 (1968).
9. J. Volc, M. Wurst and V. Musilek, *Folia Microbiol.*, 23 448 (1978).
10. Z. Diwnjak and M. D. Lilly, *Biotechnology and Bioengineering*, 18, 737–739 (1976).
11. Y. K. Cho and J. E. Bailey, *Biotechnology and Bioengineering*, 19, 769–775 (1977).

What is claimed is:

1. A method for making D-glucosone from glucose, comprising, providing an aqueous solution of glucose, and converting at least about 95% of the glucose in solution to D-glucosone in solution by enzymatic oxidation with a cell free enzyme while removing or utilizing co-produced hydrogen peroxide.

2. A method according to claim 1 wherein the D-glucosone is further converted to an end product.

3. A method according to claim 2 wherein the D-glucosone in solution is recovered as a syrup and is resolubilized in an organic solvent.

4. A method according to claim 2 wherein the end product is D-fructose.

5. A method according to claim 2 wherein the end product is 2-keto-D-gluconic acid.

6. A method according to claim 1 wherein the enzyme comprises an oxidoreductase having glucose-2-oxidase activity.

7. A method according to claim 6 wherein the enzyme is selected from the group consisting of glucose-2-oxidase from Aspergillus oryzae and pyranose-2-oxidase from Polyporus obtusus.

8. A method according to claim 6 wherein the enzyme is immobilized.

9. A method according to claim 1 wherein the hydrogen peroxide is removed by enzymatic decomposition by catalase.

10. A method according to claim 1 wherein the hydrogen peroxide is utilized in a co-process.

11. A method for making D-glucosone from glucose, comprising, providing an aqueous solution of glucose, and converting at least about 95% of the glucose in solution to D-glucosone in solution by utilizing an immobilized cell free oxidoreductase enzyme having or utilizing co-produced hydrogen peroxide, and recovering the D-glucosone in substantially pure form.

12. A method according to claim 11 which is carried out in a column reactor.

* * * * *